United States Patent [19]
Gsell

[11] Patent Number: 4,505,738
[45] Date of Patent: Mar. 19, 1985

[54] HALOVINYL-3,3-DIMETHYLCYCLO-PROPANECARBOXYLIC ACID PYRONYL ESTERS USEFUL FOR THE PROTECTION OF CULTIVATED PLANTS AGAINST THE HARMFUL EFFECTS OF HERBICIDES

[75] Inventor: Laurenz Gsell, Basel, Switzerland

[73] Assignee: Ciba-Geigy Corporation, Ardsley, N.Y.

[21] Appl. No.: 491,160

[22] Filed: May 4, 1983

[30] Foreign Application Priority Data

May 10, 1982 [CH] Switzerland ............... 2891/82

[51] Int. Cl.³ ............... A01N 43/28; C07D 309/32
[52] U.S. Cl. ............... 71/88; 549/417; 47/57.6
[58] Field of Search ............... 549/417; 71/88; 47/57.6

[56] References Cited

FOREIGN PATENT DOCUMENTS 760319  10/1956  United Kingdom.
989578   4/1965  United Kingdom.
1003477  9/1965  United Kingdom.
1003478  9/1965  United Kingdom.
1355204  6/1974  United Kingdom.
1396941  6/1975  United Kingdom.
1396942  6/1975  United Kingdom.
1403262  8/1975  United Kingdom.
1454043 10/1976  United Kingdom.

Primary Examiner—Nicky Chan
Attorney, Agent, or Firm—Frederick H. Rabin

[57] ABSTRACT

There are described novel cyclopropanecarboxylic acid derivatives of the formula I

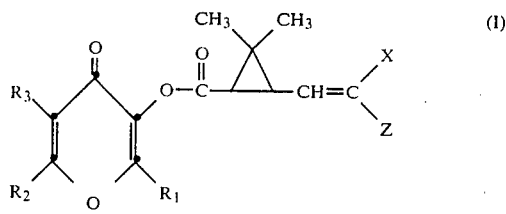

wherein $R_1$, $R_2$ and $R_3$ independently of one another are each hydrogen; halogen; $C_1$–$C_8$-alkyl which is unsubstituted or substituted by one or more substituents from the group: thiocyanogen, hydroxyl, halogen, $C_1$–$C_4$-alkoxy, $C_1$–$C_4$-alkylthio, acyloxy or $R_4$; or they are each $C_3$–$C_6$-alkenyl which is unsubstituted or substituted by $R_5$; or they are $C_3$–$C_6$-alkynyl which is unsubstituted or substituted by $R_6$; or they are $R_7$, whereby $R_4$, $R_5$, $R_6$ and $R_7$ are phenyl which is unsubstituted or substituted by a maximum of three identical or different substituents from the group: halogen, nitro, cyano, carboxylic acid, carboxylic acid alkyl ester, alkyl, alkenyl, alkynyl, haloalkyl, alkoxy or alkylthio; and X and Z are fluorine, chlorine, bromine or trifluoromethyl; and also the production of these novel derivatives. The active substances of the formula I or compositions containing them are used for protecting cultivated plants against harmful effects of agricultural chemicals.

28 Claims, No Drawings

HALOVINYL-3,3-DIMETHYLCYCLO-PROPANECARBOXYLIC ACID PYRONYL ESTERS USEFUL FOR THE PROTECTION OF CULTIVATED PLANTS AGAINST THE HARMFUL EFFECTS OF HERBICIDES

The present invention relates to novel cyclopropanecarboxylic acid derivatives, to processes for producing them, to compositions containing these cyclopropanecarboxylic acid derivatives as active ingredients, and to the use thereof for protecting cultivated plants against the harmful effects of agricultural chemicals.

With the use of agricultural chemicals, such as plant protection products, especially herbicides, the cultivated plants can to a certain extent suffer damage depending on such factors as the dosage of the agricultural chemical used and the mode of application, variety or type of cultivated plant, nature of the soil and climatic conditions, for example: exposure to light, temperature and rainfall. It is thus known for example that herbicides from the most varied classes of substances, such as triazines, urea derivatives, carbamates, thiolcarbamates, haloacetanilides, and halophenoxyacetic acids, and from other classes too, can when applied in effective amounts, damage to some degree the cultivated plants which are supposed to be protected against the disadvantageous action of undesirable plant growth. In order to overcome this problem, there have already been suggested various substances which are capable of specifically antagonising the harmful action of a herbicide on the cultivated plants, that is to say, capable of protecting the cultivated plants without at the same time noticeably affecting the herbicidal action against the weeds to be controlled. It has however been shown that the suggested antidotes frequently have only a narrow field of action, that is, a specific antidote is suitable often only for application on individual varieties of cultivated plants, and/or for the protection of the cultivated plants against individual herbicidal substances or classes of substances.

The British Patent Specification No. 1,277,557 describes for instance the treatment of seeds or shoots of wheat and sorghum with certain oxamic acid esters and amides for protection against an attack by "ALACHLOR" (N-methoxymethyl-N-chlcoroacetyl-2,6-diethylaniline). In the German Offenlegungsschriften Nos. 1,952,910 and 2,245,471, and also in the French Patent Specification No. 2,021,611, there are suggested antidotes for treating cereal, maize and rice seeds for the purpose of protecting these against the harmful effect of herbicidally active thiolcarbamates. According to the German Patent Specification No. 1,567,075 and the U.S. Pat. No. 3,131,509, hydroxyaminoacetanilides and hydantoins are used for protecting cereal seed against carbamates.

The direct pre- or post-emergence treatment of specific productive plants with antidotes, as antagonists of certain classes of herbicides, on a cultivated area of land is described in the German Offenlegungsschriften Nos. 2,141,586 and 2,218,097, and also in the U.S. Pat. No. 3,867,444.

According to the German Offenlegungsschrift No. 2,402,983, maize plants can be effectively protected against damage by chloroacetanilides by supplying the soil with an N-disubstituted dichloroacetamide as an antidote.

In addition, according to European patent application No. 11,047, it is also possible to use alkoximinobenzyl cyanides, the alkoxy group of which is substituted, inter alia, by an acetalised carbonyl group, as active ingredients for the protection of cultivated plants against the harmful action of herbicides of various classes of substances.

It has now been found that, surprisingly, a group of novel cyclopropanecarboxylic acid derivatives are excellently suitable for protecting cultivated plants against the harmful effects of agricultural chemicals, for example plant protection products, in particular herbicides. These cyclopropanecarboxylic acid derivatives are therefore designated in the following as antidotes or 'safeners'.

The novel cyclopropanecarboxylic acid derivatives of the present invention correspond to the formula I

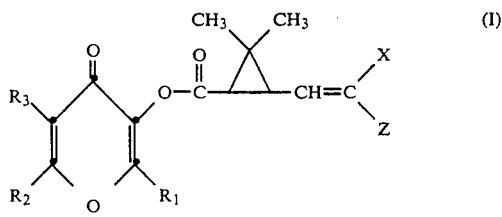

wherein $R_1$, $R_2$ and $R_3$ independently of one another are each hydrogen; halogen; $C_1$–$C_8$-alkyl which is unsubstituted or substituted by one or more substituents from the group: thiocyanogen, hydroxyl, halogen, $C_1$–$C_4$-alkoxy, $C_1$–$C_4$-alkylthio, acyloxy or $R_4$; or they are each $C_3$–$C_6$-alkenyl which is unsubstituted or substituted by $R_5$; or they are $C_3$–$C_6$-alkynyl which is unsubstituted or substituted by $R_6$; or they are $R_7$, whereby $R_4$, $R_5$, $R_6$ and $R_7$ are phenyl which is unsubstituted or substituted by a maximum of three identical or different substituents from the group: halogen, nitro, cyano, carboxylic acid, carboxylic acid alkyl ester, alkyl, alkenyl, alkynyl, haloalkyl, alkoxy or alkylthio; and X and Z are fluorine, chlorine, bromine or trifluoromethyl.

The compounds of the formula I are obtained as mixtures of various optically active isomers when homogeneous optically active starting materials are not used in the production process. By the term 'compounds of the formula I' are meant both the individual optical and geometrical isomers and the mixtures thereof. The different isomeric mixtures can be separated by known methods into the individual isomers.

By halogen, as substituent or part of a substituent, is meant in this case fluorine, chlorine, bromine or iodine.

Alkyl, as substituent or part of a substituent, embraces, within the limits of the stated number of carbon atoms in each case, all the possible isomers, for example: methyl, ethyl, n-propyl, isopropyl, n-butyl, sec-butyl, tert-butyl or isobutyl, and also pentyl, hexyl, heptyl and octyl and isomers thereof.

By alkyl, as constituent of the substituents $R_4$, $R_5$, $R_6$ and $R_7$, are meant preferably alkyl groups having 1 to 8, particularly 1 to 4, carbon atoms.

Acyloxy is in particular an unsubstituted or substituted acyclic hydrocarbon radical having a maximum of 6 carbon atoms. Alkylcarbonyloxy groups having 1 to 4 carbon atoms, especially acetoxy, are preferred.

Alkenyl, as constituent of the substituents $R_4$, $R_5$, $R_6$ and $R_7$, denotes particularly alkenyl groups having 3 to 6 carbon atoms, for example allyl and methallyl.

By alkynyl, as constituent of the substituents $R_4$, $R_5$, $R_6$ and $R_7$, are meant especially alkynyl groups having 3 to 6 carbon atoms, for example propargyl and 2-butynyl.

Preferred compounds of the formula I are those which belong to one of the groups listed below:
(a) compounds of the formula I in which $R_1$, $R_2$ and $R_3$ are as defined under the formula I, and X and Z are chlorine;
(b) compounds of the formula I in which $R_2$ has the meaning defined under the formula I, $R_1$ and $R_3$ are hydrogen, and X and Z are chlorine;
(c) compounds of the formula I in which $R_1$, X and Z are as defined under the formula I, and $R_2$ and $R_3$ are hydrogen, and
(d) compounds of the formula I in which $R_1$ is $C_1$–$C_4$-alkyl, and $R_2$ and $R_3$ are hydrogen, and X and Z have the meanings defined under the formula I.

The groups (a), (b), (c) and (d) embrace the individual isomers of the corresponding compounds, and also isomeric mixtures. Compounds particularly worth mentioning are:
2-(2,2-dichlorovinyl)-3,3-dimethyl-cyclopropanecarboxylic acid-(2-methyl-4-pyron-3-yl) ester, and
2-(2,2-dichlorovinyl)-3,3-dimethyl-cyclopropanecarboxylic acid-(2-ethyl-4-pyron-3-yl) ester.

The cyclopropanecarboxylic acid derivatives of the formula I have to a marked degree the property of protecting cultivated plants against the damaging effects of agricultural chemicals. Agricultural chemicals are for example: defoliating agents, desiccants, agents for protection against frost damage, and plant protection products, for example: insecticides, fungicides, bactericides, nematocides and especially herbicides. The agricultural chemicals can belong to various classes of substances. Herbicides can belong for example to one of the following classes: triazines and triazinones; ureas, such as 1-(benzothiazol-2-yl)-1,3-dimethylurea ("Methabenzthiazuron"), or in particular phenylureas, especially 3-(4-isopropylphenyl)-1,1-dimethylurea ("Isoproturon"), or sulfonylureas; carbamates and thiocarbamates; haloacetanilides, especially chloroacetanilides; chloroacetamides; halophenoxyacetic acid esters; diphenyl ethers, such as substituted phenoxyphenoxyacetic acid esters and -amides, and substituted phenoxypropionic acid esters and -amides; substituted pyridyloxyphenoxyacetic acid esters and -amides, and substituted pyridyloxyphenoxypropionic acid esters and -amides, in particular 2-[4-(3,5-dichloropyridyl-2-oxy)-phenoxy]-propionic acid-2-propynyl ester and 2-[4-(5-trifluoromethylpyridyl-2-oxy)-phenoxy]-propionic acid-n-butyl ester; benzoic acid derivatives; nitroanilines; oxadiazolones; phosphates; and pyrazoles.

The following are specified as examples of substances which can be used:
triazines and triazinones: 2,4-bis(isopropylamino)-6-methylthio-1,3,5-triazine ("Prometryne"), 2,4-bis(ethylamino)-6-methylthio-1,3,5-triazine ("Simetryne"), 2-(1',2'-dimethylpropylamino)-4-ethylamino-6-methylthio-1,3,5-triazine ("Dimethametryne"), 4-amino-6-tert-butyl-4,5-dihydro-3-methylthio-1,2,4-triazin-5-one ("Metribuzin"), 2-chloro-4-ethylamino-6-isopropylamino-1,3,5-triazine ("Atrazine"), 2-chloro-4,6-bis(ethylamino)-1,3,5-triazine ("Simazine"), 2-tert-butylamino-4-chloro-6-ethylamino-1,3,5-triazine ("Terbuthylazine"), 2-tert-butylamino-4-ethylamino-6-methoxy-1,3,5-triazine ("Terbumeton"), 2-tert-butylamino-4-ethylamino-6-methylthio-1,3,5-triazine ("Terbutryne"), 2-ethylamino-4-isopropylamino-6-methylthio-1,3,5-triazine ("Ametryne");

ureas: 1-(benzothiazol-2-yl)-1,3-dimethylurea; phenylureas, for example 3-(3-chloro-p-tolyl)-1,1-dimethylurea ("Chlortoluron"), 1,1-dimethyl-3-($\alpha\alpha\alpha$-trifluoro-m-tolyl)urea ("Fluometuron"), 3-(4-bromo-3-chlorophenyl)-1-methoxy-1-methylurea ("Chlorbromuron"), 3-(4-bromophenyl)-1-methoxy-1-methylurea ("Metobromuron"), 3-(3,4-dichlorophenyl)-1-methoxy-1-methylurea ("Linuron"), 3-(4-chlorophenyl)-1-methoxy-1-methylurea ("Monolinuron"), 3-(3,4-dichlorophenyl)-1,1-dimethylurea ("Diuron"), 3-(4-chlorophenyl)-1,1-dimethylurea ("Monuron"), 3-(3-chloro-4-methoxyphenyl)-1,1-dimethylurea ("Metoxuron"); sulfonylureas, for example N-(2-chlorophenylsulfonyl)-N'-(4-methoxy-6-methyl-1,3,5-triazin-2-yl)-urea, N-(2-methoxycarbonylphenylsulfonyl)-N'-(4,6-dimethylpyrimidin-2-yl)-urea, N-(2,5-dichlorophenylsulfonyl)-N'-(4,6-dimethoxypyrimidin-2-yl)-urea, N-[2-(2-butenyloxy)-phenylsulfonyl]-N'-(4-methoxy-6-methyl-1,3,5-triazin-2-yl)-urea, and also the sulfonylureas mentioned in the European Patent Publications Nos. 44808 and 44809;

carbamates and thiocarbamates: N-(3',4'-dichlorophenyl)propionanilide ("Propanil"), S-4-chlorobenzyl-diethylthiocarbamate ("Benthiocarb"), S-ethyl-N,N-hexamethylenethiocarbamate ("Molinate"), S-ethyl-dipropyl-thiocarbamate ("EPTC"), N,N-di-sec-butyl-S-benzyl-thiocarbamate, S-(2,3-dichlorallyl)-di-isopropyl-thiocarbamate ("Di-allate"), 1-(propylthiocarbonyl)-decahydro-quinaldine, S-ethyl-diisobutyl-thiocarbamate ("Butylate"), S-benzyl-diethyl-thiocarbamate;

chloroacetanilides: 2-chloro-2',6'-diethyl-N-(2''-n-propoxyethyl)-acetanilide ("Propalochlor"), 2-chloro-6'-ethyl-N-2''-methoxy-1''-methylethyl)-acet-o-toluidide("Metolachlor"), 2-chloro-2',6'-diethyl-N-(butoxymethyl)acetanilide ("Butachlor"), 2-chloro-6'-ethyl-N-(ethoxymethyl)acet-o-toluidide ("Acetochlor"), 2-chloro-6'-ethyl-N-(2''-propoxy-1''-methylethyl)acet-o-toluidide, 2-chloro-2',6'-dimethyl-N-(2''-methoxy-1''-methylethyl)acetanilide, 2-chloro-2',6'-dimethyl-N-(2''-methoxyethyl)acetanilide ("Dimethachlor"), 2-chloro-2',6'-diethyl-N-(pyrazol-1-yl-methyl)acetanilide, 2-chloro-6'-ethyl-N-(pyrazol-1-yl-methyl)acet-o-toluidide, 2-chloro-6'-ethyl-N-(3,5-dimethylpyrazol-1-ylmethyl)acet-o-toluidide, 2-chloro-6'-ethyl-N-(2''-butoxy-1''-methylethyl)acet-o-toluidide ("Metazolachlor"), 2-chloro-6'-ethyl-N-(2''-butoxyl-1''-(methylethyl)-acet-o-toluidide and 2-chloro-2'-trimethylsilyl-N-(butoxymethyl)acetanilide;

chloroacetamides: N-[1-isopropyl-2-methylpropen-1-yl-(1)]-N-(2'-methoxyethyl)-chloroacetamide;

diphenyl ethers and nitrodiphenyl ethers: 2,4-dichlorophenyl-4'-nitrophenyl ether ("Nitrofen"), 2-chloro-1-(3'-ethoxy-4'-nitrophenoxy)-4-trifluoromethyl-benzene ("Oxyfluorfen"), 2',4'-dichlorophenyl-3-methoxy-4-nitrophenyl ether ("Chlormethoxynil"), 2-[4'-(2'',4''-dichlorophenoxy)-phenoxy]-propionic acid-methyl ester, N-(2'-phenoxyethyl)-2[5'(2''-chloro-4''-trifluoromethylphenoxy)-phenoxy]-propionic acid amide, 2-[2-nitro-5-(2-chloro-4-trifluoromethylphenoxy)phenoxy]-propionic acid-2-methoxyethyl ester; 2-chloro-4-trifluoromethylphenyl-3′-oxazolin-2′-yl-4′-nitrophenyl ether;

benzoic acid derivatives: methyl-5-(2′,4′-dichlorophenoxy)-2-nitrobenzoate ("Bifenox"), 5-(2′-chloro-4′-trifluoromethylphenoxy)-2-nitrobenzoic acid ("Acifluorfen"), 2,6-dichlorobenzonitrile ("Dichlobenil");

nitroanilines: 2,6-dinitro-N,N-dipropyl-4-trifluoromethylaniline ("Trifluralin"), N-(1′-ethylpropyl)-2,6-dinitro-3,4-xylidine ("Pendimethalin");

oxadiazolones: 5-tert-butyl-3-(2′,4′-dichloro-5′-isopropoxyphenyl)-1,3,4-oxadiazol-2-one ("Oxadiazon");

phosphates: S-2-methylpiperidino-carbonylmethyl-O,O-dipropyl-phosphorodithioate ("Piperophos");

pyrazoles: 1,3-dimethyl-4-(2′,4′-dichlorobenzoyl)-5-(4′-tolylsulfonyloxy)-pyrazole; and 2-[1-(ethoxyimino)-butyl]-5-[2-(ethylthio)-propyl]-3-hydroxy-2-cyclohexen-1-one, and the sodium salt of 2-[1-(N-allyloxyamino)-butylidene]-5,5-dimethyl-4-methoxycarbonyl-cyclohexane-1,3-dione.

To be more especially emphasised is however the excellent protective action against the harmful effects of haloacetanilides, particularly chloroacetanilides, above all 2-chloro-2′,6′-diethyl-N-(2″-propoxyethyl)acetanilide and 2-chloro-6′-ethyl-N-(2″-methoxy-1″-methylethyl)-acet-o-toluidide. Likewise outstanding is the action against the thiocarbamates: S-benzyl-diethylthiocarbamate and S-4-chlorobenzyl-diethyl-thiocarbamate, and against the pyridyloxyphenoxyacetic acid ester derivative: 2-[4-(3,5-dichloropyridyl-2-oxy)-phenoxy]-propionic acid-2-propynyl ester.

Cultivated plants which can be protected by cyclopropanecarboxylic acid derivatives of the formula I against agricultural chemicals are in particular those which are of importance in the foodstuffs and textile fields, for example cultivated millet, rice, maize, varieties of cereals (wheat, rye, barley, oats, and so forth), cotton, sugar beet, sugar cane and soya bean.

The compounds of the formula I are above all excellently suitable for protecting rice plants against the harmful effects of chloroacetanilides.

A suitable process for protecting cultivated plants by the use of compounds of the formula I comprises treating cultivated plants, parts of these plants, or soils intended for the cultivation of the cultivated plants, before or after introduction of the vegetable material into the soil, with a compound of the formula I or with a composition containing such a compound. The treatment can be carried out before, simultaneously with or after the application of the agricultural chemicals. Parts of plants concerned are especially those which are capable of the new formation of a plant, for example seeds, fruits, stems and branches (cuttings), as well as roots, tubers and rhizomes.

The invention relates also to a process for the selective controlling of weeds in crops of cultivated plants, in which process the cultivated plants, parts of the cultivated plants, or cultivated areas for cultivated plants, are treated with a herbicide and a compound of the formula I, or with a composition containing this combination. The compositions which contain the herbicide/antidote combination likewise form subject matter of the present invention.

The weeds to be controlled can be both monocotyledonous and dicotyledonous weeds.

Cultivated plants or parts of these plants to be protected are for example those mentioned in the foregoing. The cultivated areas concerned are those on which cultivated plants are already growing, or sown areas of land, and also the soil intended for the growing of cultivated plants.

The amount of antidote to be applied in proportion to the amount of agricultural chemical depends largely upon the type of application. In the case of a field treatment, which is carried out either with the use of a tank mixture or with a separate application of agricultural chemical and antidote, the employed ratio of antidote to agricultural chemical is as a rule from 1:100 to 10:1, preferably 1:5 to 8:1, and particularly 1:1.

With seed dressing and similar methods of application, however, the amounts of antidote required in proportion to the amounts of agricultural chemical applied per hectare of cultivated land are much smaller. There are used for seed dressing as a rule 0.1 to 10 g of antidote per kg of seed, preferably 1 to 2 g. When the antidote is applied shortly before sowing, with seed swelling, there are advantageously used antidote solutions containing the active ingredient at a concentration of 1 to 10,000 ppm, preferably 100 to 1000 ppm.

The compounds of the formula I can be used on their own or together with inert additives and/or the agricultural chemicals to be antagonised.

The present application relates therefore also to compositions which contain compounds of the formula I and inert additives and/or agricultural chemicals to be antagonised, especially plant protection agents, in particular herbicides.

For application, the compounds of the formula I, or combinations of compounds of the formula I with the agricultural chemicals to be antagonised, are advantageously used together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions.

The formulations, that is to say, the compositions or preparations containing the active ingredient of the formula I, or a combination of active ingredient of the formula I and agricultural chemicals to be antagonised, and optionally a solid or liquid additive, are produced in a known manner, for example by the intimate mixing and/or grinding of the active ingredients with extenders, such as with solvents, solid carriers and optionally surface active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, and optionally also of the agricultural chemical to be antagonised, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-laurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, or phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"Mc Cutcheon's Detergents and Emulsifiers Annual",
  MC Publishing Corp., Ringwood, N.J., 1980, and
Sisely and Wood, "Encyclopedia of Surface Active
  Agents", Chemical Publishing Co., Inc., New York, 1980.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside. Whereas commercial products are preferably in the form of concentrated compositions, the compositions employed by the end-user are as a rule diluted.

The compositions can also contain further additives, such as stabilisers, antifoam agents, viscosity regulators, binders and adhesives, as well as fertilisers or other active substances for obtaining special effects.

For the use of compounds of the formula I, or of compositions containing them, for the protection of cultivated plants against the harmful effects of aggressive agricultural chemicals, various methods and techniques are applicable, such as those described in the following.

(i) Seed dressing (a) Dressing of the seeds with an active ingredient, formulated as a wettable powder, by shaking in a vessel until there is a uniform distribution over the surface of the seeds (dry dressing). The amount of active ingredient of the formula I used for this purpose is about 10 to 500 g (40 g to 2 kg of wettable powder) per 100 kg of seed.

(b) Dressing of the seeds with an emulsion concentrate of the active ingredient of the formula I according to method (a) (wet dressing).

(c) Dressing by immersion of the seed in a liquor containing 50–3200 ppm of active ingredient of the formula I for 1 to 72 hours, and optionally subsequent drying of the seed (immersion dressing).

The dressing of the seed or the treatment of the germinated young seedlings is, in accordance with nature, the preferred method of application, because the treatment with the active ingredient is directed completely at the target growth. There are used as a rule 10 g to 500 g, preferably 50 to 250 g of active substance (AS) per 100 kg of seed, whereby, depending on the method of treatment, which may render possible also the addition of other active substances or micronutrients, the stated limiting concentrations can be varied upwards or downwards (repeat dressing).

(ii) Application as tank mixture

A liquid preparation of a mixture of antidote and herbicide (quantitative ratio between 10:1 and 1:10) is used, the applied amount of herbicide being 0.1 to 10 kg per hectare. This tank mixture is preferably applied before or immediately after sowing, or it is worked into the unsown soil to a depth of 5 to 10 cm.

(iii) Application into the seed furrow

The antidote is introduced, as an emulsion concentrate, wettable powder or granulate, into the open sown seed furrow, and, after the covering of the seed furrow in the normal manner, the herbicide is applied before the emergence of the plants.

(iv) Controlled release of active ingredient

The active ingredient is absorbed, in solution, onto mineral granular carriers or polymerised granulates (urea/formaldehyde), and the material is allowed to dry. A coating can if required be applied (coated granules), which enables the active ingredient to be released in controlled amounts over a certain period of time.

The compounds of the formula I are produced
(a) by reacting a compound of the formula II

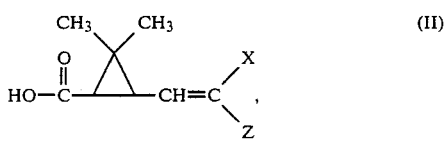

wherein X and Z are as defined under the formula I, with a compound of the formula III

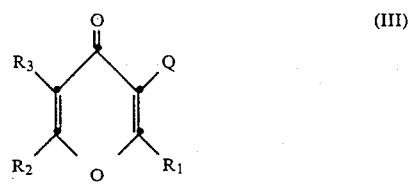

wherein $R_1$, $R_2$ and $R_3$ have the meanings given under the formula I, and Q is a nucleofug radical; or
(b) by reacting a compound of the formula IV

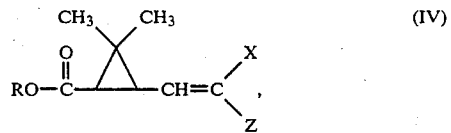

wherein X and Z are as defined under the formula I, and R is an organic radical, with a compound of the formula V

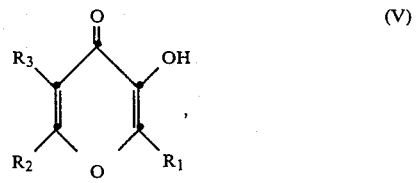

wherein $R_1$, $R_2$ and $R_3$ have the meanings given under the formula 1; or
(c) by reacting a compound of the formua VI

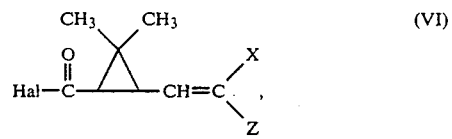

wherein X and Z are as defined under the formula I, and Hal is a halogen atom, with a compound of the formula V.

In the process variant (a), Q, as a nucleofug radical, can be for example a halogen atom or the sulfonate group —$OSO_2R'$, in which R' is for example a phenyl or naphthyl group unsubstituted or mono- or disubstituted by $C_1$–$C_4$-alkyl, or it is an aliphatic radical having a maximum of 6 carbon atoms, preferably $C_1$–$C_3$-alkyl.

In the process variant (b), the organic radical R is in particular $C_1$–$C_6$-alkyl, preferably $C_1$–$C_3$-alkyl In the starting products of the aforementioned reactions, halogen is fluorine, chlorine, bromine or iodine.

The reactions according to the process variants (a) and (c) are performed in the presence of a base. Suitable bases are for example: slightly basic inorganic salts, such as potassium carbonate; or preferably organic bases, for example pyridine, quinoline, methylpiperidine, dimethylaniline or triethylamine.

The transesterification according to process variant (b) is carried out advantageously in the presence of a basic transesterification catalyst. Suitable catalysts are for example: sodium or potassium hydroxide or sodium or potassium alcoholates, especially sodium or potassium alkylates having 1 to 4 carbon atoms, for example sodium ethylate.

The reactions according to process variants (a), (b) and (c) can be performed in a temperature range of $-20°$ to $+200°$ C. In the case of process variant (b), the reactants are advantageously heated in the presence of a basic transesterification catalyst. The reaction according to process variant (c) can be easily carried out at room temperature. A temperature range of between $-20°$ and $+25°$ C. is advantageously used for this reaction.

The starting products employed in the aforementioned process variants (a), (b) and (c) are known, or they can be produced by methods analogous to known methods.

The following Examples serve to further illustrate the invention.

EXAMPLE 1

2-(2,2-dichlorovinyl)-3,3-dimethyl-cyclopropanecarboxylic acid-(2-methyl-4-pyron-3-yl) ester 3.78 g of 3-hydroxy-2-methyl-4-pyrone and 7.5 g of 2-(2,2-dichlorovinyl)-3,3-dimethyl-cyclopropanecarboxylic acid chloride (85% cis, 15% trans) are dissolved in 100 ml of toluene, and 2.9 ml of pyridine in 10 ml of toluene are added dropwise at 15° C. over a period of 10 minutes. After the addition of 0.1 g of 4-dimethylaminopyridine, the reaction mixture is stirred at 50° C. for 6 hours. The solution is cooled, and is then successively washed with water, 2N HCl and 5% NaHCO$_3$; it is subsequently dried, and concentrated by evaporation. The yield is 8.3 g of 2-(2,2-dichlorovinyl)-3,3-dimethyl-cyclopropanecarboxylic acid-(2-methyl-4-pyron-3-yl) ester as a cistrans isomeric mixture having 85% cis-form and 15% transform; m.p. <50° C.

By recrystallisation from ether/pentane is obtained the pure cis form of 2-(2,2-dichlorovinyl)-3,3-dimethyl-cyclopropanecarboxylic acid-(2-methyl-4-pyron-3-yl) ester; m.p. 79°–83° C.

By a method analogous to any one of the methods described in the foregoing, there are also obtained the following compounds of the formula I which are listed in Table 1 together with the compound of the above Example.

TABLE 1

| No. | R₁ | R₂ | R₃ | X | Z | configuration % cis | % trans | Physical data |
|-----|----|----|----|----|----|----|----|----|
| 1 | CH₃ | H | H | Cl | Cl | 85 | 15 | m.p. <50° C. |
| 2 | CH₃ | H | H | Cl | Cl | 100 | 0 | m.p. 79–83° C. |
| 3 | CH₃ | H | H | Cl | Cl | 0 | 100 | m.p. 136–137° C. |
| 4 | C₂H₅ | H | H | Cl | Cl | 85 | 15 | $n_D^{21}$ 1,5385 |
| 5 | CH₃ | H | H | Br | Br | mixture | | |
| 6 | CH₃ | H | H | F | F | mixture | | m.p. 85–86° C. |
| 7 | CH₃ | H | H | Cl | Cl | 100 | 0 | |
| 8 | H | —CH₂OH | H | Cl | Cl | 85 | 15 | |
| 9 | H | —CH₂SCN | H | Cl | Cl | 85 | 15 | |
| 10 | H | —CH₂OCOCH₃ | H | Cl | Cl | 85 | 15 | |

Formulation Examples for liquid active ingredients of the formula I (%=percent by weight)

| 2. Emulsion concentrates | a | b | c |
|---|---|---|---|
| active ingredient from Table 1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 3. Solutions | a | b | c | d |
|---|---|---|---|---|
| active ingredient from Table 1 | 80% | 10% | 5% | 95% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 4. Granulates | a | b |
|---|---|---|
| active ingredient from Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 5. Dusts | a | b |
|---|---|---|
| active ingredient from Table 1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (%=percent by weight)

| 6. Wettable powders | a | b | c |
|---|---|---|---|
| active ingredient from Table 1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 7. Emulsion concentrate | |
|---|---|
| active ingredient from Table 1 | 10% |
| octylphenol polyethylene glycol ether (4–5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| 8. Dusts | a | b |
|---|---|---|
| active ingredient from Table 1 | 5% | 8% |
| talcum | 95% | — |
| kaolin | — | 92% |

Dusts ready for use are obtained by mixing the active ingredient with the carriers and grinding the mixture in a suitable mill.

| 9. Extruder granulate | |
|---|---|
| active ingredient from Table 1 | 10% |
| sodium lignin sulfonate | 2% |
| carboxymethylcellulose | 1% |

-continued

| 9. Extruder granulate | |
|---|---|
| kaolin | 87% |

The active ingredient is mixed and ground with the additives, and the mixture is moistened with water. This mixture is extruded and subsequently dried in a stream of air.

| 10. Coated granulate | |
|---|---|
| active ingredient from Table 1 | 3% |
| polyethylene glycol (M G 200) | 3% |
| kaolin | 94% |

The finely ground active ingredient is evenly applied, in a mixer, to the kaolin moistened with polyethylene glycol. Dustfree coated granules are obtained in this manner.

| 11. Suspension concentrate | |
|---|---|
| active ingredient from Table 1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

Biological Examples

EXAMPLE 12

Test with antidote and herbicide on transplanted rice; application method: tank mixture Rice plants are grown to the 1½-2-leaf stage in soil. The plants are then transplanted in bunches (3 plants together in each case) in sandy loam in a container (47 cm long, 29 cm wide and 24 cm high). The surface of the soil is subsequently covered with water to a depth of 1.5-2 cm. Two to three days after transplantation, there is applied as a tank mixture, directly into the water, 2-chloro-2',6'-diethyl-N-(2''-propoxyethyl)-acetanilide ("Pretilachlor") as herbicide, together with 2-(2,2-dichlorovinyl)-3,3-dimethyl-cyclopropanecarboxylic acid-(2-methyl-4-pyron-3-yl) ester as the antidote. An assessment is made, 24 days after transplantation, of the protective action of the antidote as a percentage. The plants treated with the herbicide alone (no protective action) and the completely untreated control plants (=100% growth) provide reference values. The results are shown in Table 2.

TABLE 2

| Applied amount kg/ha | | Relative |
|---|---|---|
| herbicide | antidote | protective action % |
| 1.0 | 1.0 | 50 |
| 0.75 | 0.75 | 50 |
| 0.5 | 0.5 | 38 |

EXAMPLE 13

Test with antidote and herbicide on transplanted rice plants; application method: root treatment Rice plants of the Yamabiko variety are grown to the 1½-2-leaf stage in soil, and are then washed out. The plants are immersed in bunches (3 plants together in each case) up to just the top of the roots, for 15 to 60 minutes, in a solution of 2-(2,2-dichlorovinyl)-3,3-dimethyl-cyclopropanecarboxylic acid-(2-methyl-4-pyron-3-yl) ester, as the antidote, at a concentration of 10 and 100 ppm, respectively. These plants are subsequently transplanted to sandy loam in containers (47 cm long, 29 cm wide and 24 cm deep), and the surface of the soil is covered with water to a depth of 1.5-2 cm. Two to three days after transplantation, 2-chloro-2',6'-diethyl-N-(2''-propoxyethyl)-acetanilide ("Pretilachlor") is applied as herbicide directly into the water. An assessment is made, 10 and 24 days after transplantation, of the protective action of the antidote as a percentage. The plants treated with the herbicide alone (no protective action) and the completely untreated control plants (=100% growth) provide reference values. The results are summarised in Table 3.

TABLE 3

| Applied amount | | Relative |
|---|---|---|
| herbicide kg/ha | antidote ppm | protective action in % |
| 0.75 | 100 | 38 |
|  | 10 | 25 |
| 0.5 | 100 | 25 |
|  | 10 | 12.5 |

EXAMPLE 14

Test with antidote and herbicide on rice plants sown in water; application method: tank mixture Rice seeds are pre-swelled for 48 hours in water. Plastics containers (each 25 cm long, 17 cm wide and 12 cm high) are filled with soil, into which the pre-swelled rice seeds are sown. There is subsequently applied by spraying as a tank mixture: 2-chloro-2',6'-diethyl-N-(2''-propoxyethyl)-acetanilide ("Pretilachlor"), as the herbicide, together with 2-(2,2-dichlorovinyl)-3,3-dimethyl-cyclopropanecarboxylic acid-(2-methyl-4-pyron-3-yl) ester as the antidote. The level of the water is progressively raised corresponding to the growth of the rice plants. An assessment is made, 18 days after sowing, of the protective action of the antidote as a percentage. The plants treated with the herbicide alone (no protective action) and the completely untreated control plants (=100% growth) provide reference values. The results are summarised in Table 4.

TABLE 4

| Applied amount kg/ha | | Relative |
|---|---|---|
| herbicide | antidote | protective action % |
| 1.0 | 1.0 | 38 |
|  | 0.5 | 25 |
|  | 0.25 | 25 |
| 0.75 | 0.75 | 50 |
|  | 0.375 | 38 |
|  | 0.187 | 12.5 |
| 0.5 | 0.5 | 50 |
|  | 0.25 | 50 |
|  | 0.125 | 63 |
|  | 0.06 | 25 |

EXAMPLE 15

Test with antidote and herbicide on rice sown dry; application method: tank mixture Rice seeds of the IR-36 variety are sown in containers (each 47 cm long, 29 cm wide and 24 cm high); the seeds are covered and lightly tamped. There is subsequently applied by spraying as a tank mixture: 2-chloro-2',6'-diethyl-N-(methoxymethyl)-acetanilide ("Alachlor"), as the herbicide, together with 2-(2,2-dichlorovinyl)-3,3-dimethylcyclopropanecarboxylic acid-(2-methyl-4-pyron-3-yl) ester as the antidote. About 20 days after sowing (3-leaf stage of the rice plants), the surface of the soil is covered with water to a depth of 4 cm. An assessment is made, 30 days after sowing, of the protective action of the antidote as a percentage. The plants treated with the herbicide alone (no protective action) and the completely untreated control plants (=100% growth) provide reference values. The results are summarised in Table 5.

TABLE 5

| Applied amount kg/ha | | Relative |
| --- | --- | --- |
| herbicide | antidote | protective action in % |
| 0.25 | 0.25 | 38 |
| 0.125 | 0.125 | 25 |

EXAMPLE 16

Test with antidote and herbicide on rice sown dry; application: seed dressing

Rice seeds are mixed together, in a glass container, with 2-(2,2-dichlorovinyl)-3,3-dimethyl-cyclopropanecarboxylic acid-(2-methyl-4-pyron-3-yl) ester as the antidote. Seeds and antidote are thoroughly mixed by shaking and rotation. Containers (each 47 cm long, 29 cm wide and 24 cm high) are then filled with sandy loam, and the dressed seeds are sown therein. After the seeds have been covered over, 2-chloro-6'-ethyl-N-(2''-methoxy-1''-methylethyl)-acet-o-toluidide ("Metolachlor") is applied as the herbicide, as a dilute solution, to the surface of the soil. After 20 days after sowing (3-leaf stage of the rice plants), the surface of the soil is covered with water to a depth of 4 cm. An assessment is made, 30 days after the application of the herbicide, of the protective action of the antidote as a percentage. The plants treated with the herbicide alone (no protective action) and the completely untreated control plants (=100% growth) provide reference values. The results are summarised in Table 6.

TABLE 6

| Applied amount | | Relative |
| --- | --- | --- |
| herbicide kg/ha | antidote g/kg of seed | protective action in % |
| 1.0 | 4 | 38 |
| 1.0 | 1 | 25 |
| 0.75 | 4 | 38 |
| 0.5 | 1 | 25 |

EXAMPLE 17

Seed swelling, rice; herbicide in the pre-emergence process

Rice seeds are soaked for 48 hours in solutions of the substance to be tested as antidote at a concentration of 100 ppm, and the seeds are then left to dry for about two hours until they no longer stick together. Plastics containers (length × width × height = 25 × 17 × 12 cm) are filled to 2 cm below the top edge with sandy loam. The pre-swelled seeds are sown on the surface of the soil in each container, and only slightly covered with soil, the soil being maintained in a moist (not muddy) state. The herbicide: 2-chloro-2',6'-diethyl-N-[2''-(n-propoxy)-ethyl]-acetanilide is then applied as a dilute solution to the surface of the soil. The water level is successively raised to correspond with the growth of the plants. The protective action of the antidote is estimated in percent 18 days after application of the herbicide. The plants treated with the herbicide alone (no protective action) and the completely untreated control plants (=100% growth) provide reference values. The results are summarised in Table 7.

TABLE 7

| Antidote compound No. | Antidote ppm | Herbicide kg of AS/ hectare | Relative protective action in % |
| --- | --- | --- | --- |
| 1 | 100 | 0.25 | 63 |
| 3 | 100 | 0.25 | 25 |
| 4 | 100 | 0.25 | 25 |

EXAMPLE 18

Seed dressing, rice; herbicide in the pre-emergence process

Rice seeds of the IR-36 variety are placed together with 2-(2,2-dichlorovinyl)-3,3-dimethyl-cyclopropanecarboxylic acid-(2-methyl-4-pyron-3-yl) ester, as antidote, into a glass container, and are thoroughly mixed by shaking and rotation. Plastics containers (length × width × height = 47 × 29 × 24 cm) are filled with sandy loam, and the dressed seeds are sown therein. After the seeds have been covered with soil, the herbicide: 2-chloro-6'-ethyl-N-(2''-methoxy-1''-methylethyl)-acet-o-toluidide ("Metolachlor") is sprayed onto the surface of the soil. The protective action of the antidote is estimated in percent 18 days after sowing. The plants treated with the herbicide alone (no protective action) and the completely untreated control plants (=100% growth) provide reference values. The results are summarised in Table 8.

TABLE 8

| Antidote g of AS/kg of seed | Herbicide kg of AS/ hectare | Relative protective action in % |
| --- | --- | --- |
| 4 | 1.0 | 38 |
| 4 | 0.75 | 38 |

EXAMPLE 19

Test with antidote and herbicide on transplanted rice plants; application method: mixing into the soil The antidote: 2-(2,2-dichlorovinyl)-3,3-dimethylcyclopropanecarboxylic acid-(2-methyl-4-pyron-3-yl) ester is mixed into the soil, contained in cultivation trays, at a concentration of 10 and 100 ppm, respectively. After a period of 2 days, rice plants are grown to the 1½-2-leaf stage in the cultivation trays. The plants are then transplanted, in bunches (3 plants together in each case), to sandy loam in containers (length × width × height = 47 × 29 × 24 cm), and the surface of the soil is covered with water to a depth of 1.5-2 cm. Two to three days after transplantation, the herbicide: S-4- chlorobenzyldiethyl-thiocarbamate ("Benthiocarb") is applied directly into the water. The protective action of the antidote is estimated in percent 24 days after transplantation. The plants treated with the herbicide alone (no protective action) and the completely untreated control plants (=100% growth) provide reference values. The results are summarised in Table 9.

TABLE 9

| Antidote ppm | Herbicide kg/ha | Relative protective action in % |
|---|---|---|
| 100 | 8 | 50 |
| 10 | 8 | 25 |

EXAMPLE 20

Test with antidote and herbicide on transplanted rice plants; application method: immersion bath (drench method)

Rice plants of the Yamabiko variety are grown to the 1½-2-leaf stage in cultivation trays. One to two days before transplantation, the whole cultivation tray containing the rice plants is immersed in each case in a larger tray containing an aqueous solution of 2-(2,2-dichlorovinyl)-3,3-dimethyl-cyclopropanecarboxylic acid-(2-methyl-4-pyron-3-yl) ester as the antidote. The plants are then transplanted, in bunches (3 plants in each bunch), to sandy loam in containers (length × width × height = 47 × 29 × 24 cm), and the surface of the soil is covered with water to a depth of 1.5-2 cm. Two to three days after transplantation, the herbicide: S-4-chlorobenzyl-diethyl-thiocarbamate is applied directly into the water. The protective action of the antidote is estimated in percent 24 days after transplantation. The plants treated with the herbicide alone (no protective action) and the completely untreated control plants (=100% growth) provide reference values. The results obtained in this test are summarised in Table 10.

TABLE 10

| Antidote ppm | Herbicide kg/ha | Relative protective action in % |
|---|---|---|
| 100 | 8 | 25 |

EXAMPLE 21

Tank mixture in the post-emergence process on wheat

Wheat seeds of the "Farnese" variety are sown, in a greenhouse, in plastics pots (upper diameter 11 cm) each containing 0.5 liter of soil. After the seeds have been covered with soil, the substance to be tested as antidote and the herbicide: 2-[4-(3,5-dichloropyridyl-2-oxy)-phenoxy]-propionic acid-2-propynyl ester are applied together as a tank mixture in the post-emergence process. The protective action of the antidote is estimated in percent 20 days after application. The plants treated with herbicide alone and the completely untreated control plants provide reference data. The results are summarised in the following Table 11.

TABLE 11

| Antidote compound No. | Antidote kg of AS/ hectare | Herbicide kg of AS/ hectare | Relative protective action in % |
|---|---|---|---|
| 1 | 1.5 | 0.75 | 50 |

TABLE 11-continued

| Antidote compound No. | Antidote kg of AS/ hectare | Herbicide kg of AS/ hectare | Relative protective action in % |
|---|---|---|---|
| 4 | 1.5 | 0.75 | 50 |

EXAMPLE 22

Tank mixture on maize in the pre-emergence process

Maize seeds of the "LG 5" variety are sown, in a greenhouse, in plastics pots (upper diameter 11 cm) each containing 0.5 liter of soil. After the seeds have been covered with soil, there is applied as a tank mixture, to the surface of the soil: 2-(2,2-dichlorovinyl)-3,3-dimethyl-cyclopropanecarboxylic acid-(2-methyl-4-pyron-3-yl)-ester as the antidote, together with 2-chloro-2',6'-dimethyl-N-(2''-methoxy-1''-methylethyl)-acetanilide as the herbicide. The protective action of the antidote is estimated in percent 21 days after application. The plants treated with the herbicide alone and the completely untreated control plants provide referance data. The results are summarised in the following Table 12.

TABLE 12

| Antidote kg of AS/ hectare | Herbicide kg of AS/ hectare | Relative protective action in % |
|---|---|---|
| 2.0 | 2.0 | 25 |
| 1.0 | 2.0 | 38 |

EXAMPLE 23

Test with herbicide and antidote on sorghum (millet); application method: tank mixture in the pre-emergence process Plastics containers (length × width × height = 47 × 17 × 12 cm) are filled with sandy loam, and sorghum seeds of the "Funk G 522" variety are sown therein. After the seeds have been covered with soil, there is applied as a tank mixture to the surface of the soil: 2-(2,2-difluorovinyl)-3,3-dimethyl-cyclopropanecarboxylic acid-(2-methyl-4-pyron-3-yl) ester as the antidote, together with the herbicide: 2-chloro-6'-ethyl-N-(2''-methoxy-1''-methylethyl)-aceto-o-toluidide ("Metolachlor"), as a dilute solution. The protective action of the antidote is estimated in percent 30 days after application. The plants treated with the herbicide alone (no protective action) and the completely untreated control plants (100% growth) provide reference data. The results are summarised in the following Table 13.

TABLE 13

| Antidote kg/ha | Herbicide kg/ha | Relative protective action in % |
|---|---|---|
| 1.5 | 1.5 | 50 |

What is claimed is:
1. A compound of the formula I

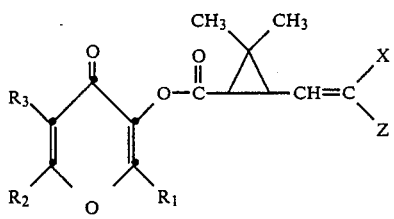

wherein $R_1$, $R_2$ and $R_3$ independently of one another are each hydrogen; halogen; $C_1$-$C_8$-alkyl which is unsubstituted or substituted by one or more substituents from the group: thiocyanogen, hydroxyl, halogen, $C_1$-$C_4$-alkoxy, $C_1$-$C_4$-alkylthio, acyloxy or $R_4$; or they are each $C_3$-$C_6$-alkenyl which is unsubstituted or substituted by $R_5$; or they are $C_3$-$C_6$-alkynyl which is unsubstituted or substituted by $R_6$; or they are $R_7$, whereby $R_4$, $R_5$, $R_6$ and $R_7$ are phenyl which is unsubstituted or substituted by a maximum of three identical or different substituents from the group: halogen, nitro, cyano, carboxylic acid, carboxylic acid alkyl ester, alkyl, alkenyl, alkynyl, haloalkyl, alkoxy or alkylthio; and X and Z are fluorine, chlorine, bromine or trifluoromethyl.

2. A compound of the formula I according to claim 1, wherein X and Z are chlorine.

3. A compound of the formula I according to claim 2, wherein, $R_1$ and $R_3$ are hydrogen.

4. A compound of the formula I according to claim 1, wherein $R_2$ and $R_3$ are hydrogen.

5. A compound of the formula I according to claim 4, wherein $R_1$ is $C_1$-$C_4$-alkyl.

6. 2-(2,2-Dichlorovinyl)-3,3-dimethyl-cyclopropanecarboxylic acid-(2-methyl-4-pyron-3-yl) ester.

7. 2-(2,2-Dichlorovinyl)-3,3-dimethyl-cyclopropanecarboxylic acid-(2-ethyl-4-pyron-3-yl) ester.

8. A composition for the protection of cultivated plants against harmful effects of herbicides, which composition contains, as at least one active ingredient, an effective amount of a compound of the formula I according to claim 1.

9. A composition according to claim 8, which contains 0.1 to 99 percent by weight of active ingredient of the formula I, and 1 to 99.9 percent by weight of a solid or liquid additive, including 0 to 25 percent by weight of a tenside.

10. A composition according to claim 9, which contains 0.1 to 95 percent by weight of active ingredient of the formula I, 5 to 99.8 percent by weight of a solid or liquid additive, and 0.1 to 25 percent by weight of a tenside.

11. A composition according to claim 8, which contains a compound of the formula I together with a herbicide.

12. A composition according to claim 11, which contains a chloroacetanilide as herbicide.

13. A composition according to claim 12, which contains 2-chloro-2',6'-diethyl-N-(2''-propoxyethyl)-acetanilide as herbicide.

14. A composition according to claim 12, which contains 2-chloro-6'-ethyl-N-(2''-methoxy-1''-methylethyl)-acet-o-toluidide as herbicide.

15. A composition according to claim 11, which contains 2-[4-(3,5-dichloropyridyl-2-oxy)-phenoxy]-propionic acid-2-propynyl ester as herbicide.

16. A composition according to claim 11, which contains S-benzyl-diethyl-thiocarbamate as herbicide.

17. A composition according to claim 11, which contains S-4-chlorobenzyl-diethyl-thiocarbamate as herbicide.

18. A process for protecting cultivated plants against harmful effects of herbicides, which process comprises treating the cultivated plants, parts of these plants, or soils intended for the growing of cultivated plants with an effective amount of a compound of the formula I according to claim 1.

19. A process according to claim 18 for protecting cultivated plants against harmful effects of chloroacetanilides.

20. A process according to claim 19 for protecting cultivated plants against harmful effects of 2-chloro-2',6'-diethyl-N-(2''-propoxyethyl)-acetanilide.

21. A process according to claim 19 for protecting cultivated plants against harmful effects of 2-chloro-6'-ethyl-N-(2''-methoxy-1''-methylethyl)-acet-o-toluidide.

22. A process according to claim 18 for protecting cultivated plants against harmful effects of 2-[4-(3,5-dichloropyridyl-2-oxy)-phenoxy]-propionic acid-2-propynyl ester.

23. A process according to claim 18 for protecting cultivated plants against harmful effects of S-benzyl-diethyl-thiocarbamate.

24. A process according to claim 18 for protecting cultivated plants against harmful effects of S-4-chlorobenzyl-diethyl-thiocarbamate.

25. A process according to claim 18 for protecting rice plants.

26. A process for selectively controlling weeds in crops of cultivated plants, which process comprises treating the cultivated plants, parts of these plants, or soils intended for growing cultivated plants, with a herbicide and an effective dose of a compound of the formula I, according to claim 1, as antidote.

27. A process according to claim 26 for selectively controlling weeds in crops of cultivated millet, rice, maize, wheat, rye, barley, oats, cotton, sugar beet, sugar cane and soya bean.

28. A method for protecting cultivated plants against harmful effects of agricultural chemicals, which method comprises applying to the cultivated plants or to the locus thereof an effective amount of a compound of the formula I according to claim 1.

* * * * *